(12) United States Patent
Fukui et al.

(10) Patent No.: US 6,277,395 B1
(45) Date of Patent: Aug. 21, 2001

(54) SWALLOWING-ASSISTIVE DRINK

(75) Inventors: Atsuko Fukui, Yotsukaido; Masanori Nakajima, Chiba; Takashi Kamijima, Ina; Mika Ohta, Kamiina, all of (JP)

(73) Assignee: Ryukakusan Co. Ltd., Tokyo (JP)

( * ) Notice: Subject to any disclaimer, the term of this patent is extended or adjusted under 35 U.S.C. 154(b) by 0 days.

(21) Appl. No.: 09/524,247

(22) Filed: Mar. 13, 2000

(51) Int. Cl.$^7$ .................................................. A61K 47/00
(52) U.S. Cl. .................... 424/439; 424/451; 424/464; 424/489
(58) Field of Search .................... 426/573, 577, 426/578, 590; 424/439, 451, 464, 489

(56) References Cited

U.S. PATENT DOCUMENTS

| | | | |
|---|---|---|---|
| 3,978,243 | * | 8/1976 | Pedersen ........................ 426/573 |
| 4,639,374 | * | 1/1987 | Matsunobu et al. ............ 426/43 |
| 5,597,595 | * | 1/1997 | DeWille et al. ................ 426/74 |
| 5,861,048 | * | 1/1999 | Kamasaka et al. ............. 71/11 |
| 5,932,235 | | 8/1999 | Ninomiya et al. . |

FOREIGN PATENT DOCUMENTS

| | | | |
|---|---|---|---|
| 356023875A | * | 3/1981 | (JP) . |
| 6-38693 | | 2/1994 | (JP) . |
| 7-309745 | | 11/1995 | (JP) . |
| 7-116049 | | 12/1995 | (JP) . |
| 8-175971 | | 4/1996 | (JP) . |
| 9-187233 | | 7/1997 | (JP) . |

* cited by examiner

Primary Examiner—Thurman K. Page
Assistant Examiner—Liliana Di Nola-Baron
(74) Attorney, Agent, or Firm—Mark B. Garred; Stetina Brunda Garred & Brucker

(57) ABSTRACT

To provide a swallowing-assistive drink for medicines that improves swallowing various medicines, is convenient and substitutable with ordinary drinking water, and does not disturb the efficacy of medicines and a swallowing method.

A swallowing-assistive drink for helping swallowing medicines that contains water and an adhesive paste, forming a viscous liquid or a gelatinoid. If the drink is viscous liquid, the viscosity is 1,000–25,000 cP at 20° C., and if the drink is gelatinous, jelly strength is 10–100 g/cm$^2$ at 20° C.

14 Claims, 15 Drawing Sheets

Plunger diameter 2cm (3.14Cm$^2$)

Press rate 10mm/sec

Clearance 5mm

Measurement Temperature 20 °C

コップゼリー : with a Cup of jelly (according to the invention)

水 : with Water

水 : with Water

水 : with Water

SWALLOWING-ASSISTIVE DRINK

BACKGROUND OF THE INVENTION

1. Field of the Invention

The present invention relates to a swallowing-assistive drink for medicines, more particularly, to a swallowing-assistive drink which facilitates or helps swallowing medicines without difficulty and without giving foreign body sensation to patients, infants and aged persons who have difficulty when taking medicines in swallowing them with ordinary drinking water because of accompanying some pain (such as a bitter taste) owing to various diseases, infirmity or even in healthy people.

2. Description of the Prior Art

Medicines for internal use are generally taken orally with water or tea. However, patients, especially aged persons or the like are difficult to swallow such medicines with water or tea. They sometimes could not swallow well to be choked or left the medicine in their mouth when taking medicines in dosage forms of powders, granules, tablets or the like. Therefore, a sufficient therapeutic effect was not obtained, and further the patient had discomfort.

Although crashing tablets or mixing medicines into food such as boiled rice, miso soup or juice has thus been conducted when taking medicines, this is time-consuming and troublesome. Moreover, this procedure of crashing tablets sometimes resulted in not giving an expected therapeutic effect because the releasing-time of ingredients of medicine could not be controlled and masking of taste could not be performed and so on.

In order to cope with these problems, small tablets, jelly and decomposable tablets are designed as to dosage forms. Further for foods, additive powder for liquid foods which thicken the liquid foods (miso soup or the like) to make them to be swallowed easily is on the market.

However, there were problems that design only on dosage form as mentioned above can not lead sufficient effect and that the swallowing-improving agents for medicines have not yet been developed although there are some for liquid foods.

BRIEF SUMMARY OF THE INVENTION

Objects of the Invention

The present invention has been conducted considering these problems of prior arts. An object of the present invention is to provide a swallowing-assistive drink for medicines that improves swallowing various medicines, being convenient and substitutable for ordinary water, moreover, not disturbing the efficacy of medicines, and a swallowing method.

SUMMARY OF THE INVENTION

The present inventors made various studies on a drink that facilitates swallowing medicines orally taken in order to solve the problems described above, formed that the above problems could be solved by mixing a specific adhesive paste with water and accomplished the present invention.

In the words, a swallowing-assistive drink of the present invention is an assistive- drink to facilitate swallowing medicines characterized in that it contains water and an adhesive paste to make viscous liquid or gelatinoid.

In addition, a swallowing method of the present invention is characterized by taking medicines together with the swallowing-assistive drink as mentioned above.

Operation

The swallowing-assistive drink of the present invention has an appropriate jelly strength or viscosity.

Accordingly, patients who have difficulty in swallowing medicines because of infirmity or various diseases besides healthy people can easily swallow various medicines by use of the present inventive swallowing-assistive drink without affecting the efficacy of the medicines.

Further, the swallowing-assistive drink of the present invention also has a function of enwrapping various kinds of medicines. Therefore, in those who have declined contractive strength of the muscle around the throat or stricture of the esophagus owing to the muscle strain, the feeling of the foreign substance can be reduced, leading to swallowing without choking, by use of the swallowing-assistive drink.

Specifically, owing to this enwrapping-function, highly water-soluble powder is enwrapped securely and hardly eluted at room temperature; as for solid formulations, the number of the medicine at a dose can be increased.

Further, such enwrapping-function makes medicine-masking possible. For example, the present swallowing-assistive drink functions as a bitter-taste mask, being convenient for infants or the like to take medicines.

Furthermore, in spite of having the enwrapping-function described above, the present swallowing-assistive drink neither affects on disintegration or dissolution of medicines nor causes interaction with medicines because a major ingredient of the drink is water; therefore, it does not disturb therapeutic effects of various medicines.

Moreover, the present swallowing-assistive drink is a low-calorie and non-sugar drink not affecting insulin metabolism; so that it can be also used safely in diabetic patients and it hardly causes caries even when using just before bedtime.

In addition, since the present swallowing-assistive drink is a simple drink containing water and an adhesive paste as essential components with excellent stability, it is easy to carry it if it is filled in a small container or the like, being convenient when patients go out.

DETAILED DESCRIPTION OF THE PREFERRED EMBODIMENTS

Figure 1:
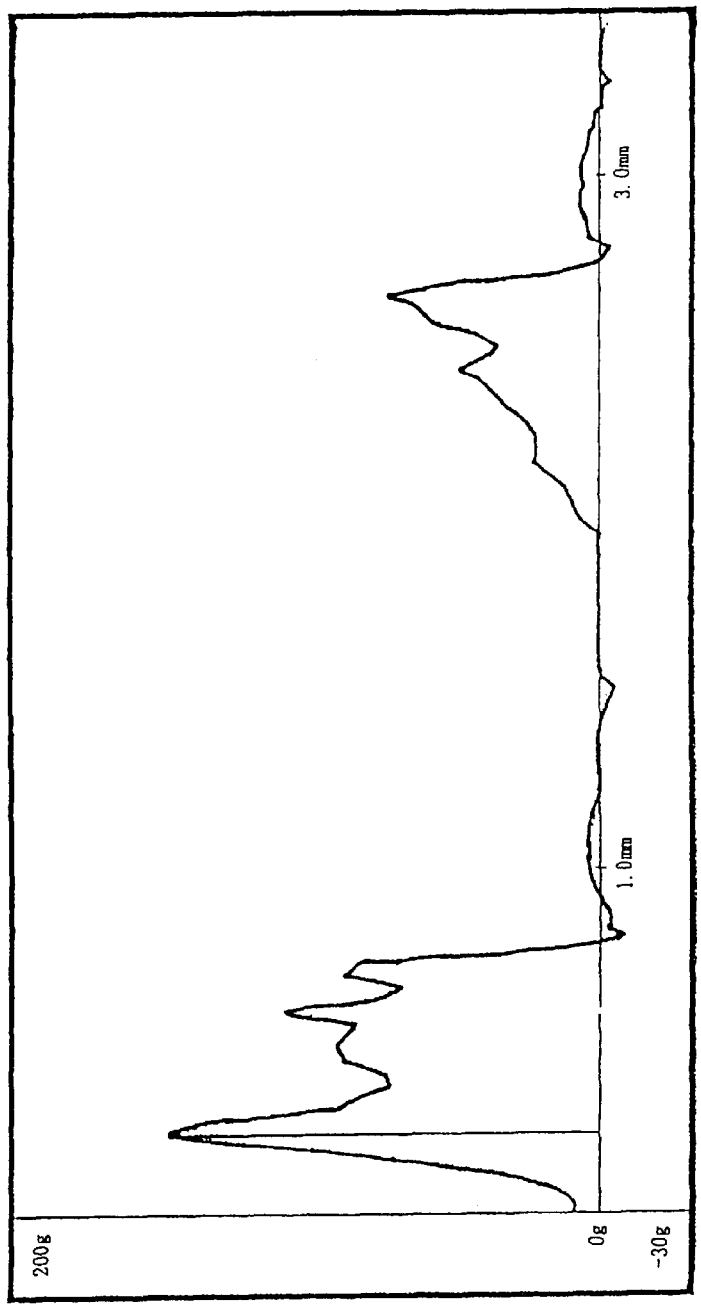
FIG. 1 is a characteristic graph showing the results of measurement by a rheometer for the swallowing-assistive drink in Example 1.

The swallowing-assistive drink of the present invention is illustrated in detail as follows.

As mentioned above, the swallowing-assistive drink contains water and an adhesive paste.

According to the present invention, water suitable for drinking is sufficient as water component and tapwater, various types of ion-exchange water, purified water or the like can be mentioned.

An adhesive paste may be any substance that can be mixed with water almost homogeneously to give viscosity or facilitate gelation. Specifically the following can be mentioned: agar, carrageenan, gellan gum, furcellaran, gelatin, pectin, curdlan, locust bean gum, tara gum, guar gum, xanthan gum, arginic acid, arginates, azotobacter vinelandi gum, cassia gum, psyllium seed gum, tamarind gum, CMCNa (carboxymethylcellulose Na), CMCCa, whey protein, starch or modified starch and their optional mixtures.

The swallowing-assistive drink of the present invention is a mixture of water and an adhesive paste as mentioned above, and takes forms of viscous liquid to gelatinoid at room temperature. Specifically, the viscosity at 20° C. is preferably 1,000–25,000 cP if it is a viscous liquid, and the jelly strength at 20° C. is preferably 10–100 g/cm$^2$ if it is a gelatinoid.

If the jelly strength is less than 10 g/cm$^2$ or the viscosity is less than 1,000 cP, misswallowing is apt to occur in swallowing medicines. On the other hand, if the jelly strength exceeds 100 g/cm$^2$ or the viscosity exceeds 25,000 cP, swallowing becomes difficult for those who have difficulty in swallowing. Thus both cases are unpreferable.

Further, the content of the adhesive paste described above can be optionally selected considering the types of adhesive paste and the viscosity range described above, and may be typically 0.1–5.0 wt % to the total amount of the swallowing-assistive drink.

Water may be typically account for 80.0–99.9 wt %.

In addition, the swallowing-assistive drink of the present invention may contain additives such as gelation accelerators and sugars for a source of nutrition besides essential components, water and an adhesive paste, as long as it exhibits an effect of swallowing improvement which the present invention is intended.

For example, 0.2–2.0 wt % citric acid, and 0.1–0.2 wt % trisodium citrate can be added as a gelation accelerator, and 8–10 wt % sugars, such as mannitol, erythritol and glucose, can be added. As for sugars, those which diabetic patients can take are preferable. Further, 0.2–0.5 wt % dextrin may be added as a gelation adjuvant.

Next, a preparation method for the swallowing-assistive drink is illustrated.

The swallowing-assistive drink of the present invention can be obtained by dissolving an appropriate adhesive paste in an appropriate amount of heating water followed by addition of a gelation accelerator, a gelation enhancer, sugars, and other additives with dissolving by heating and stirring.

Dissolution temperature can optionally be altered, typically 80–100° C. when dissolving by heating.

Further, the swallowing-assistive drink obtained as mentioned above can be taken together with various medicines: after keeping medicines in a mouth, the swallowing-assistive drink maybe poured into the mouth instead of water and swallowed together with the medicines or after premixing of the medicines with the swallowing-assistive drink, the obtained mixture (liquid) may be poured into the mouth and swallowed.

As mentioned above, the swallowing-assistive drink of the present invention is applied to various kinds of medicines, preferably applied especially for the medicines which have been considered difficult to be swallowed.

Medicines having such difficulty in being swallowed, are tablets having a diameter exceeding 10 mm and capsules having a size larger than No. 1. According to the present swallowing-assistive drink, even such tablets and capsules can be smoothly swallowed because they are enwrapped by the present swallowing-assistive drink having appropriate viscosity or the like as mentioned above.

Further, because granules and powders are stuck between false teeth and on a mucous membrane in the mouth or entered in the trachea, swallowing these often becomes difficult. By using the swallowing-assistive drink of the present invention, even such granule and powder formulations can be readily swallowed because the granules or the like are enwrapped with the present swallowing-assistive drink to prevent sticking in the mouth or the like.

Also, after use, the swallowing-assistive drink gives almost no remnant feeling in the mouth such as that given by soft drinks, but it leaves a light aftertaste. Therefore, it can be used preferably especially by false teeth users.

In addition, as for medicines having strong odors or bitter tastes, the dislike to the smells or bitter tastes sometimes leads to difficulty in swallowing. Even such medicines can be readily swallowed because of being enwrapped and masked by the present swallowing-assistive drink.

Besides, even the powder formulation in this case is prevented from being stuck in the mouth or the like as mentioned above, therefore it gives no problem of leaving unpleasant smells or bitter tastes.

Moreover, using the present swallowing-assistive drink makes it easier to take solid and powder formulations in mixture, which has been known to be difficult in swallowing.

Embodiment

The following examples are given to further illustrate the present invention. However, it should be understood that the present invention is not limited by these examples.

Embodiment 1

The gelatinated swallowing-assistive drink of the present example was obtained by dissolving polysaccharides, pectin, carrageen in, xanthan gum and agar, in a fixed amount of water with heating followed by adding other additives into this mixture to dissolve them with heating at 80° C. and stirring. The formulation for blending is illustrated in detail as follows.

| Component | Blending quantity (pont by weight) |
|---|---|
| Agar | 0.20 |
| Locust bean gum | 0.05 |
| Pectin | 0.04 |
| Carrageenin | 0.02 |
| Xanthan gum | 0.01 |
| Citric acid | 0.21 |
| Trisodium citrate | 0.14 |
| Erythritol | 8.82 |
| Flavor | 0.10 |
| Purified water | 90.41 |
| Total amount | 100.00 (pont by weight) |

As shown in the above formulation, the swallowing-assistive drink obtained is almost composed of water, and it neither affects disintegration of medicines nor exhibits interaction with medicines. Further, this has a refreshing taste with suppressing a sweet taste being suitable for taking.

The jelly strength of this swallowing-assistive drink was measured using a rheometer (Sun Science Company made, trade name: RHEOMETER MODEL COMPAC-100), and the result obtained is shown in FIG. 1.

Herein, the said jelly strength is calculated as follows.

After charging the swallowing-assistive drink into a sample container placed on an elevating stand, the elevating stand is raised to contact the charged swallowing-assistive drink with a cylindrical plunger placed on the upper side, further the raising is continued at a fixed press rate to break through the plunger, then stopped at a fixed clearance. Next, the elevating stand is descended, while the resistant value (load) is measured, as well as the descending displacement. The jelly strength is calculated from the load value according to the following equation:

Jelly strength=Maximum load (g)/Plunger area (cm$^2$).

In this Embodiment, the swallowing-assistive drink was charged up to 15 mm in a sample container having a bottom of 40 mm in diameter. The plunger was 2 cm in diameter, the press rate was 10 mm/sec, the clearance was 5 mm, and the measurement temperature was 20° C.

The jelly strength of the swallowing-assistive drink in this Embodiment was 46.6 g/cm$^2$, since the maximum load was 146 g and the plunger area was 3.14 cm$^2$ according to FIG. 1.

Embodiment 2

Figure 2:
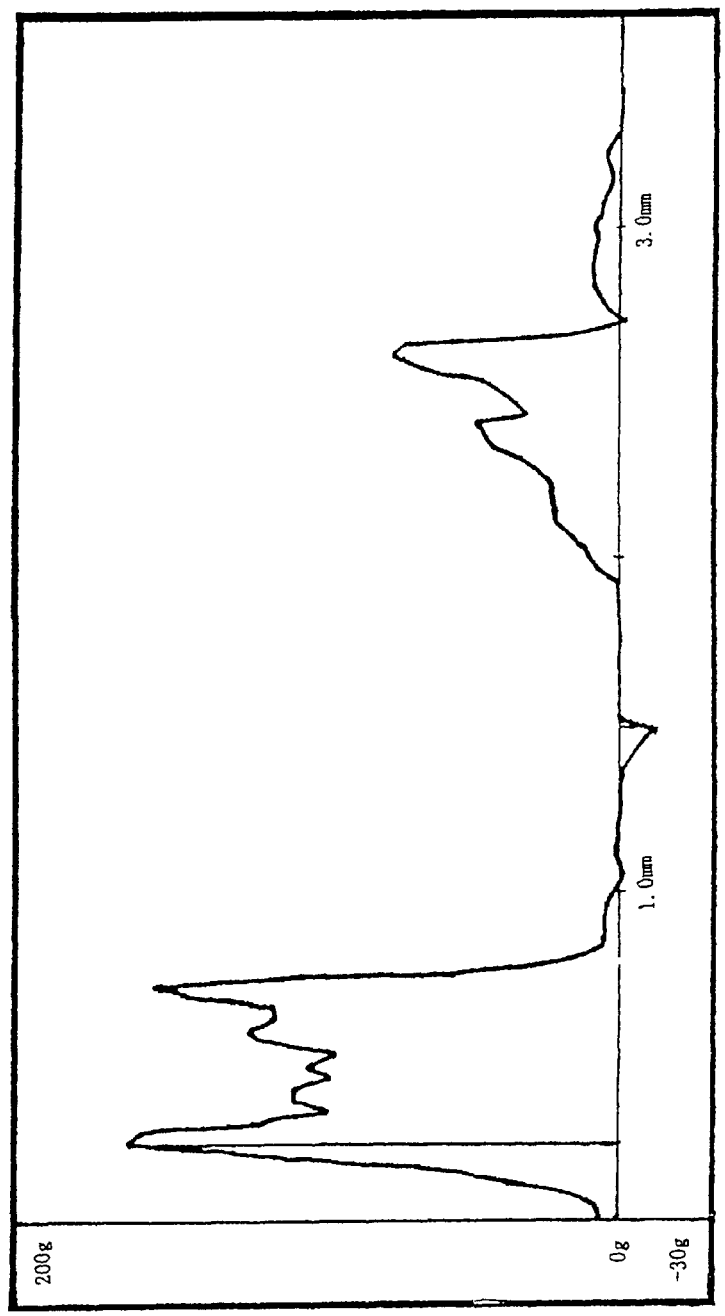
FIG. 2 is a characteristic graph showing the results of measurement by a rheometer for the swallowing-assistive drink in Example 2.

The swallowing-assistive drink of the present invention was obtained by repetition of the procedure similar to Embodiment 1 except for using the following formulation for blending. The jelly strength was measured similarly to Embodiment 1, and the result was shown in FIG. 2. The jelly strength of the swallowing-assistive drink in the present Embodiment was 51.9 g/cm$^2$.

| Component | Blending quantity (pont by weight) |
|---|---|
| Agar | 0.20 |
| Locust bean gum | 0.05 |
| Pectin | 0.04 |
| Carrageenan | 0.02 |
| Xanthan gum | 0.01 |
| Citric acid | 0.21 |
| Trisodium citrate | 0.14 |
| Mannitol | 8.81 |
| Flavor | 0.10 |
| Purified water | 90.42 |
| Total amount | 100.00 (pont by weight) |

Embodiment 3

The swallowing-assistive drink of the present Embodiment was obtained as a viscous liquid by dissolving polysaccharides, guar gum and starch as adhesive pastes, in a fixed amount of water with other additives. The formulation for blending was illustrated in detail as follows.

| Component | Blending quantity (pont by weight) |
|---|---|
| Guar gum | 1.00 |
| Starch | 1.00 |
| Citric acid | 0.21 |
| Trisodium citrate | 0.14 |
| Erythritol | 8.81 |
| Flavor | 0.20 |
| Purified water | 88.64 |
| Total amount | 100.00 (pont by weight) |

The viscosity of this swallowing-assistive drink was measured using a B-type rotational viscometer (Shibaura System Company made: trade name Vismetron VS-A) to show a value of 10,000 cP. Herein, the viscosity was calculated as follows. After setting the temperature of the swallowing-assistive drink at 20° C., it was rotated using a No. 4 rotator at 12 rpm, and the readings after 2 min was multiplied by a multiplier to give viscosity values.

Embodiment 4

Xanthan gum and starch as adhesive paste were dissolved in a fixed amount of water with other additives and the swallowing-assistive drink in this Embodiment was obtained as a viscous liquid. The formulation for blending is illustrated in detail as follows.

| Component | Blending quantity (pont by weight) |
|---|---|
| Xanthan gum | 0.50 |
| Starch | 1.50 |
| Citric acid | 0.21 |
| Trisodium citrate | 0.14 |
| Erythritol | 8.81 |
| Flavor | 0.20 |

-continued

| Component | Blending quantity (pont by weight) |
| --- | --- |
| Purified water | 88.64 |
| Total amount | 100.00 (pont by weight) |

The viscosity of this swallowing-assistive drink was measured similarly to Embodiment 3, showing a value of 8,500 cP.

Test Example 1

The enwrapping-function of the swallowing-assistive drink of the present invention was investigated. Namely, the swallowing-assistive drink obtained in Embodiment 1 was charged into Petri dishes at room temperature followed by addition of water-soluble granules to this mixture, then the condition was observed. The result obtained is shown in FIG. 3.

Figure 3:
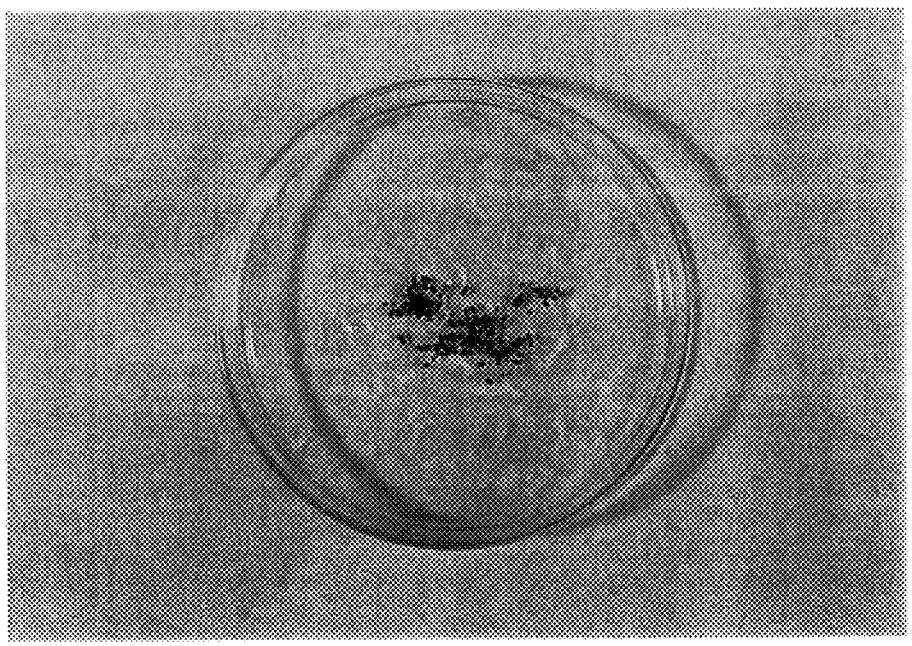
FIG. 3 is a photograph showing the condition obtained by adding highly water-soluble granules into the swallowing-assistive drink.
Figure 4:
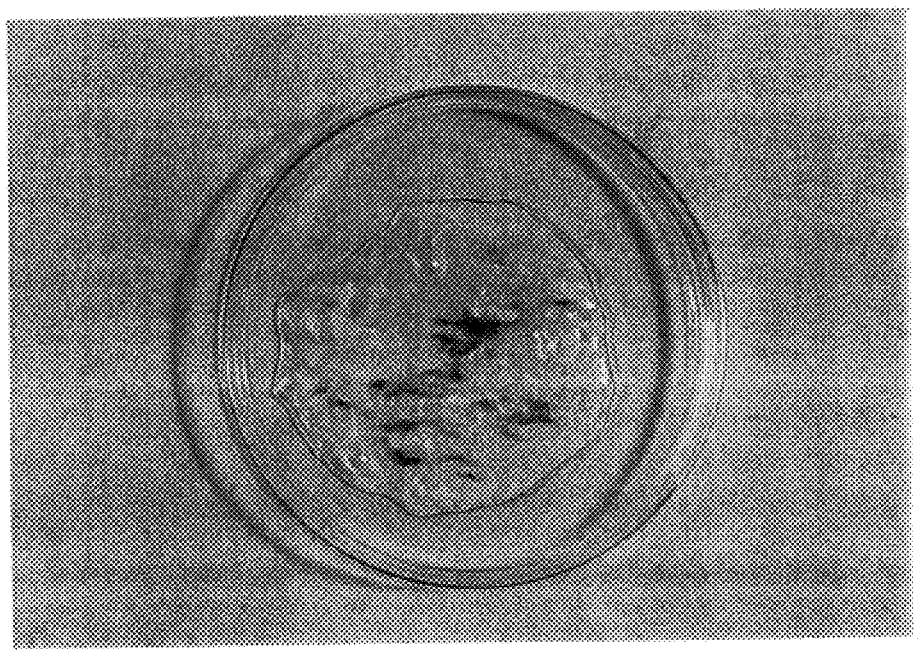
FIG. 4 is a photograph showing the condition obtained by lightly stirring the condition of FIG. 3.
Figure 5:
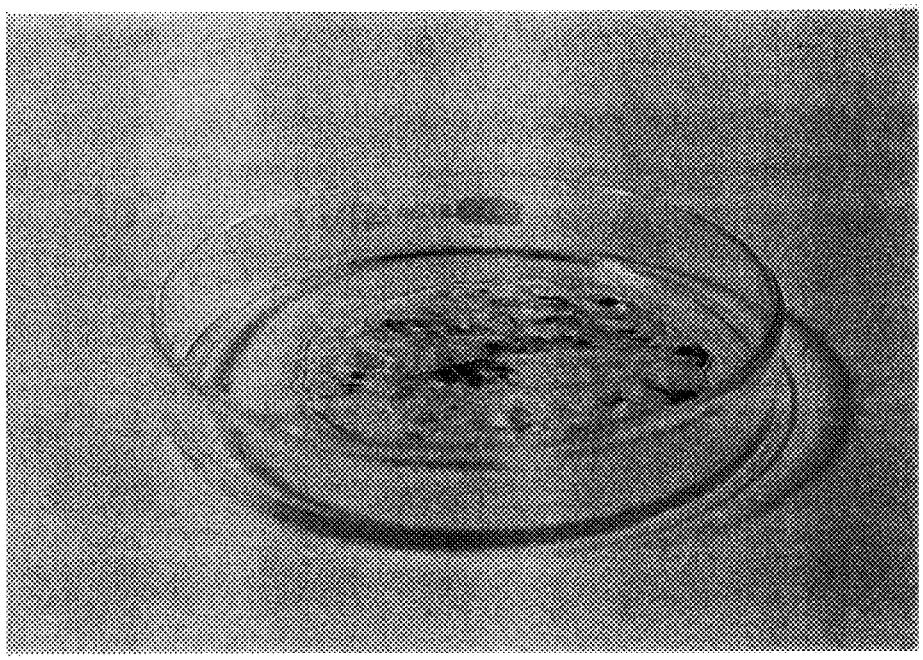
FIG. 5 is a photograph of FIG. 4 from a different angle.

In addition, after slightly stirring the mixture in the condition shown in FIG. 3, changes in condition was observed. The result is shown in FIG. 4. Further, FIG. 5 shows the condition of FIG. 4 from a different angle.

Furthermore, observation similar to that mentioned above was conducted by changing an amount of the above swallowing-assistive drink and the highly water-soluble granules. The results obtained are shown in FIG. 6 and 7 (after stirring).

Test Example 2
[Comparative Test on drinking water]

Figure 8:
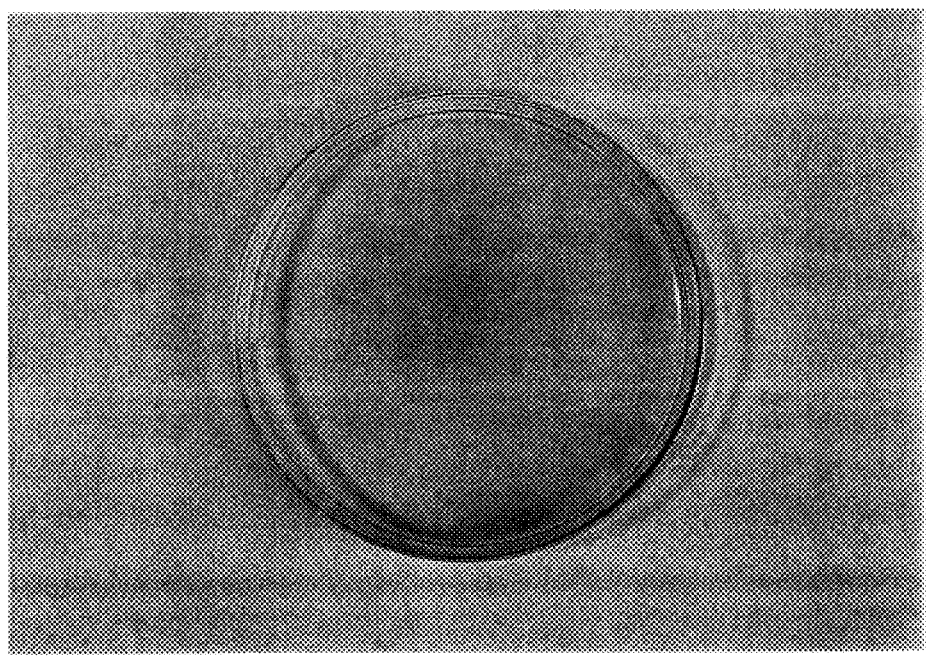
FIG. 8 is a photograph showing the condition obtained by adding highly water-soluble granules into drinking water.

After filling drinking water, in place of the swallowing-assistive drink, in Petri dishes followed by addition of highly water-soluble granules similarly to Test Example 1, the condition was observed. The result obtained is shown in FIG. 8.

Figure 6:
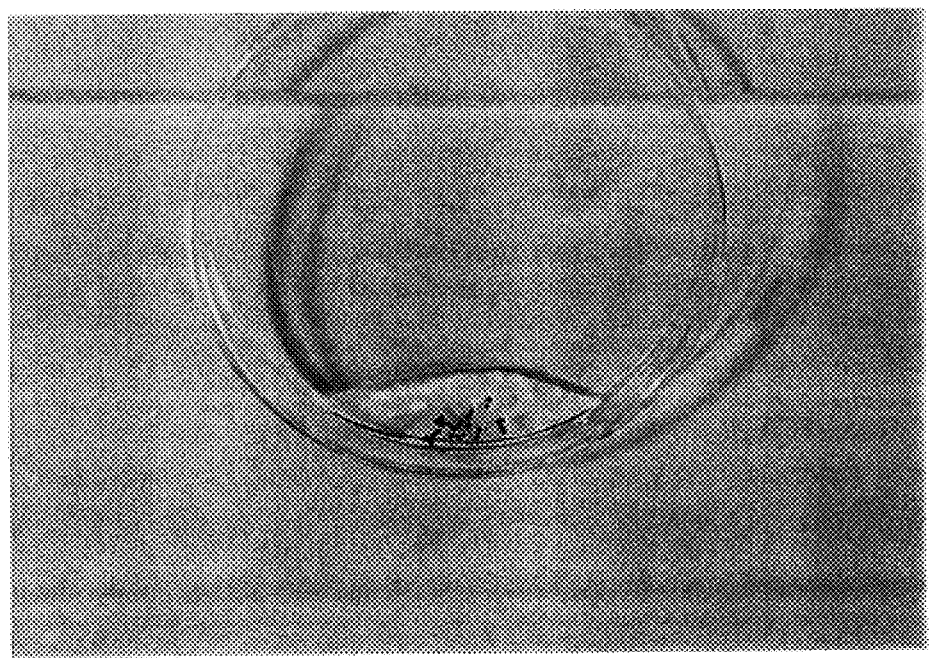
FIG. 6 is a photograph showing the condition obtained by adding highly water-soluble granules into the swallowing-assistive drink.
Figure 7:
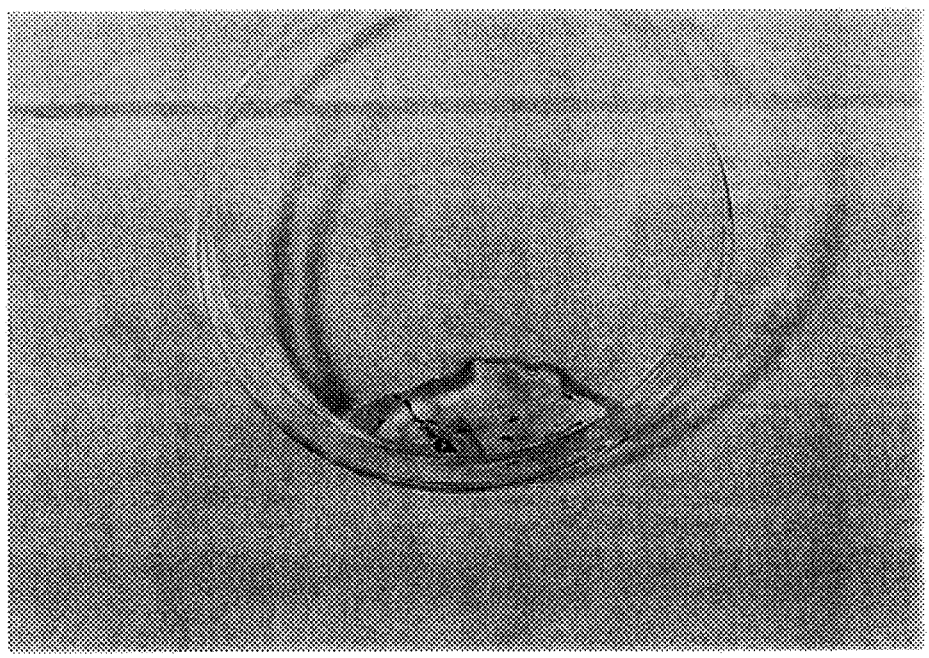
FIG. 7 is a photograph showing the condition obtained by slightly stirring the mixture of FIG. 6.

The results of Test Examples 1 and 2 obviously show that the swallowing-assistive drink of the present invention has an excellent enwrapping-function which is not shown by drinking water and that this function is maintained after slightly stirring: in FIGS. 3 and 6, highly water-soluble granules are neither dissolved nor dispersed and maintain its intact form; also in FIGS. 4, 5 and 7, the granules are dissolved and scarcely enwrapped.

Thus, the swallowing-assistive drink of the present invention can enwrap appropriately even highly water-soluble granules and powders. Therefore, the drink can make it easy to take granules or the like, because it can as prevent the granules from sticking in the mouth and it can also agglutinate them.

Further, the enwrapping-function mentioned above similar to that of a wafer can mask such bitter tastes of medicines. Therefore, it makes it easy to take medicines and is extremely suitable because bitter tastes or the like do not remain.

In addition, the present swallowing-assistive drink does not disturb the disintegration and dissolution of medicines in the body because the viscosity of the present swallowing-assistive drink decreases when being heated up to the body temperature (37° C.) to lose its enwrapping function.

Test Example 3

The following tests were conducted on the swallowing-assistive drink of Embodiments 1 and 2; the subject patients were composed of 12 women and 20 men, 32 in all, aged 75–85 with the average age of 78.

The evaluation was also conducted by asking for opinions of the subjects themselves and findings obtained by observations of nurses about the swallowing-assistive effect when taking medicines with the swallowing-assistive drinks of Embodiments 1 and 2. The evaluation was made in the following 5 levels:

1. Good, 2. Fairly good, 3. Neither good nor bad, 4. Fairly bad, and 5. Bad.

The medicines for internal usewere 8 capsules, 16 tablets, 4 granule formulations and 4 powder formulations. The resulting evaluation is that all the finding by 32 patients and all the findings by the nurses are "good." The impressions of the patients and the nurses in this case are shown as follows.
[Impressions of patients and nurses]
1. Although tablets and powders had been taken separately so far, they could be taken together at once by the use of the present swallowing-assistive drinks.
2. Mixing the present swallowing-assistive drinks with medicines led to the feeling like their being enwrapped with a wafer without dissolving to be jelly, giving a good touch in the mouth and easiness of taking medicines.
3. Mixing powders of Chinese medicines with the present swallowing-assistive drinks prevented the bitter taste from spreading in the mouth and made it easy to take them.
4. Tablets could be taken without choking.
5. Using them for swallowing the medicines with strong bitter tastes led to making the bitter taste mild even when those who did not particularly have problems in swallowing.
6. When taking Chinese medicines and powders, using the present swallowing-assistive drinks led to easier taking than taking them enwrapped with wafers.

Test Example 4

The following test was conducted on the swallowing-assistive drink of Embodiment 1.

First, the purpose of this test was explained to a patient (the age of 75, man) who had difficulty in swallowing when taking medicines with water, and his consent was acquired.

Next, barium powder was filled up in a No. 2 capsule and the capsule was used as a placebo. The placebo was taken by the patient with about 20 ml of the swallowing-assistive drink of the present invention, while fluoroscopic video-radiographs of the conditions of taking this medicine were taken by scanning from the mouth to the stomach of the patient. The image information obtained was put into a personal computer and the time-course changes were analyzed as still image data of two sheets a second. The result is shown in FIG. 9.

Further, the still pictures of "Cup jelly 02," "Cup jelly 03," "Cup jelly 04," "Cup jelly 09,"

Figure 9:
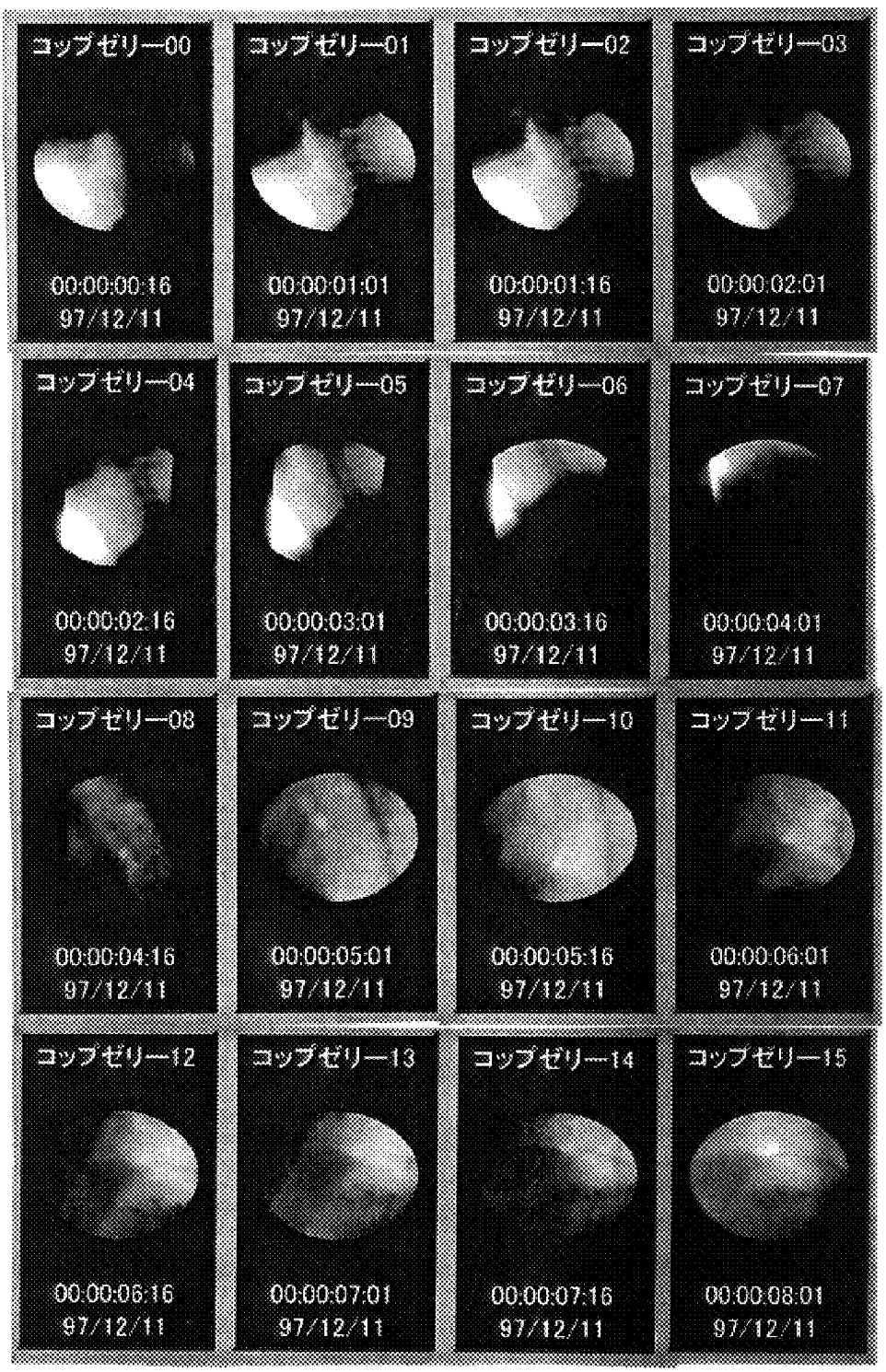
FIG. 9 shows still picture data showing conditions of taking in Test Example 4.
Figure 10:
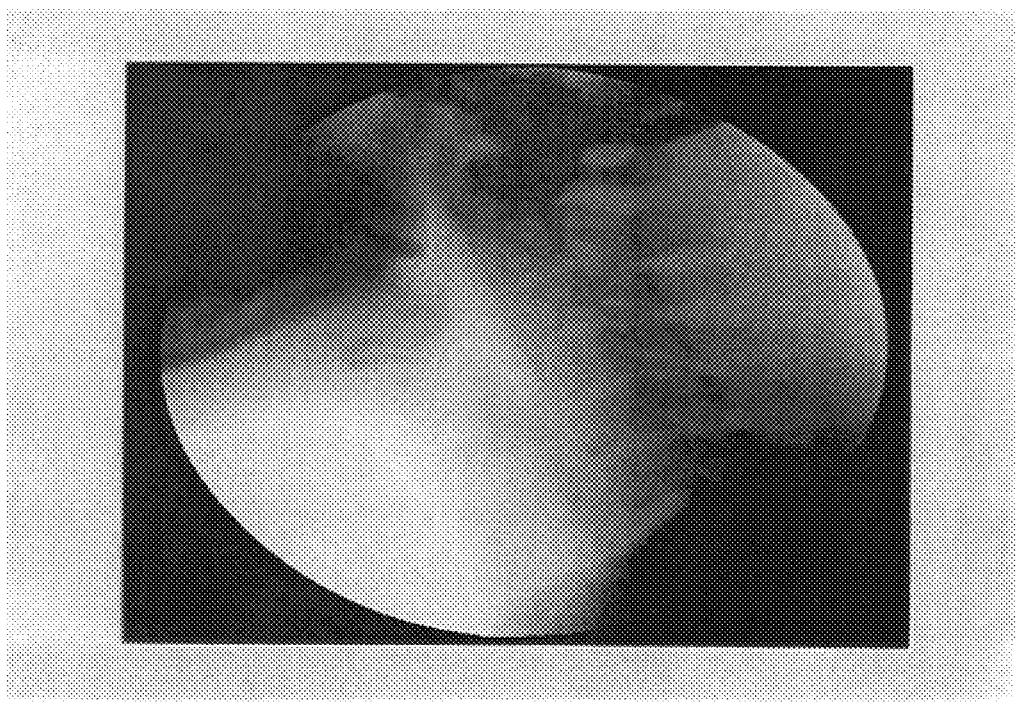
FIG. 10 is a partly enlarged view of FIG. 9.
Figure 11:
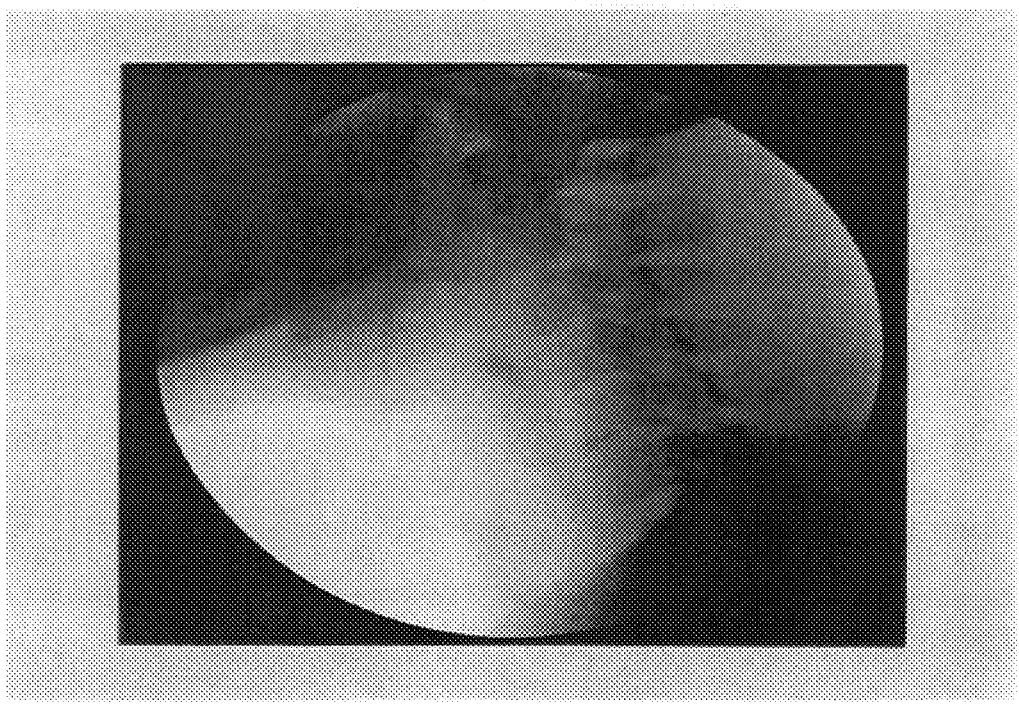
FIG. 11 is a partly enlarged view of FIG. 9.
Figure 12:
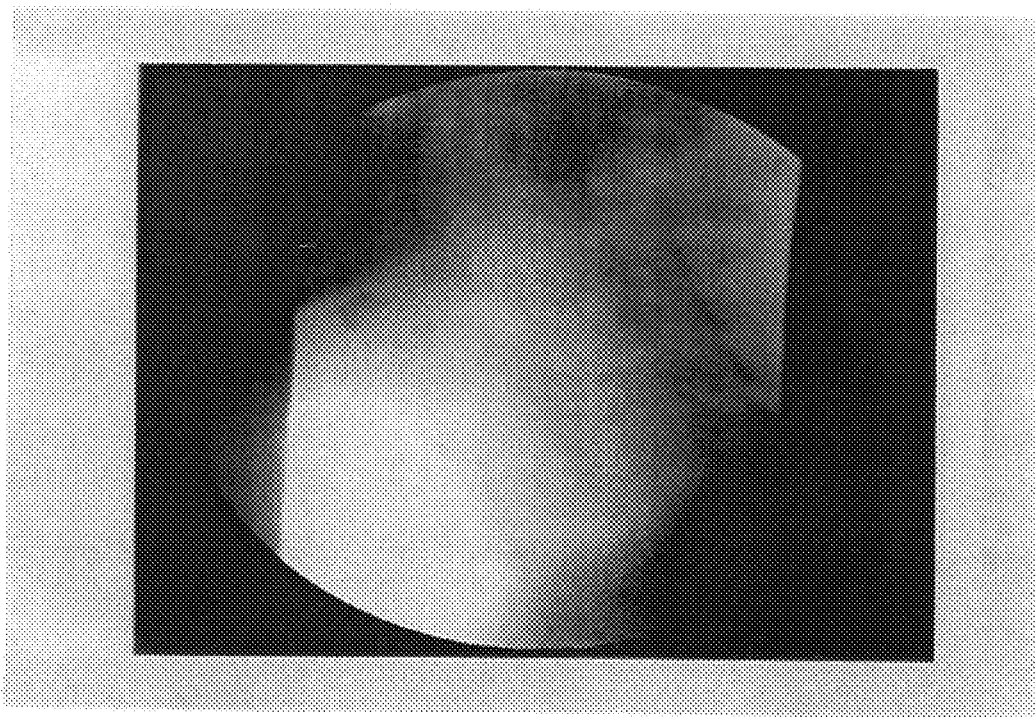
FIG. 12 is a partly enlarged view of FIG. 9.
Figure 13:
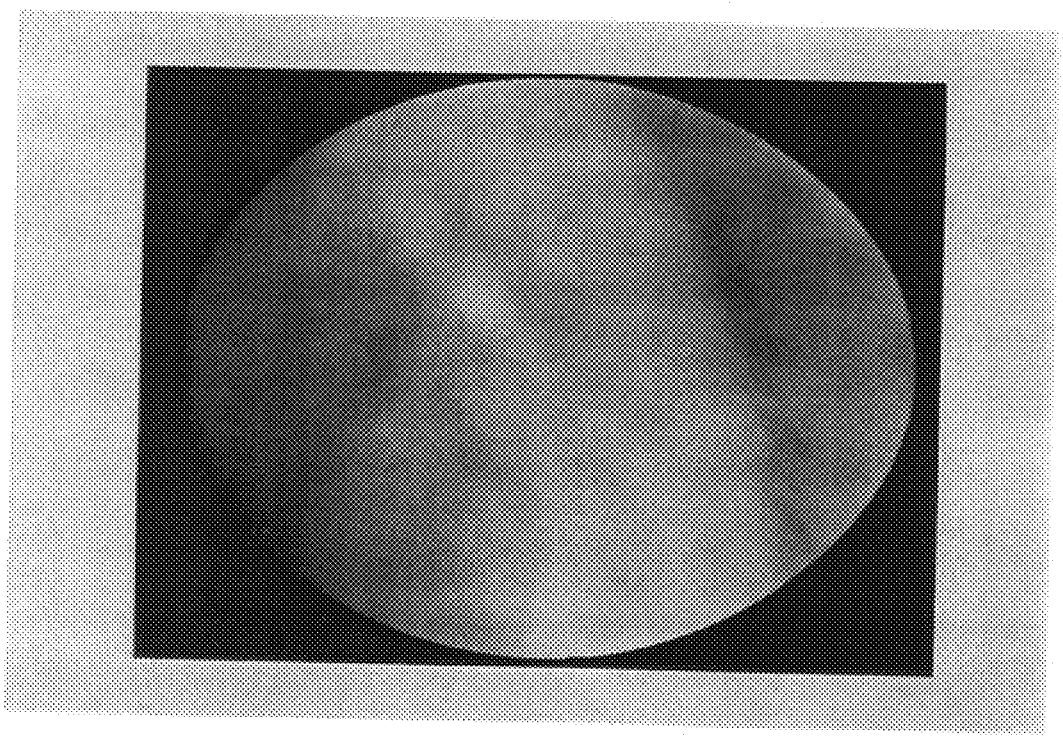
FIG. 13 is a partly enlarged view of FIG. 9.
Figure 14:
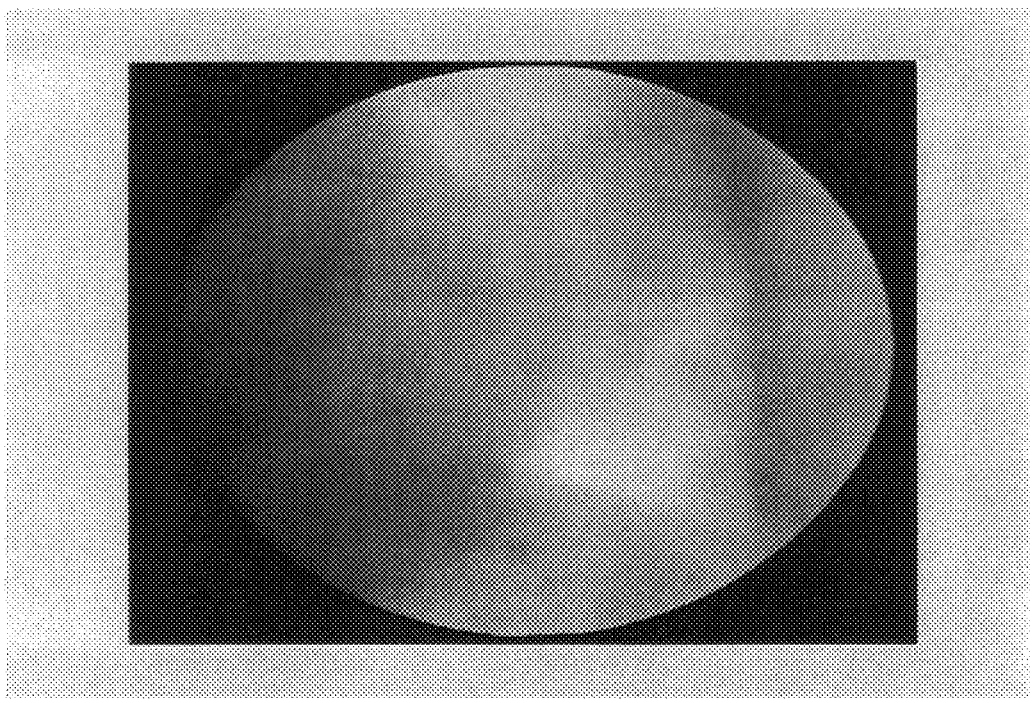
FIG. 14 is a partly enlarged view of FIG. 9.
Figure 15:
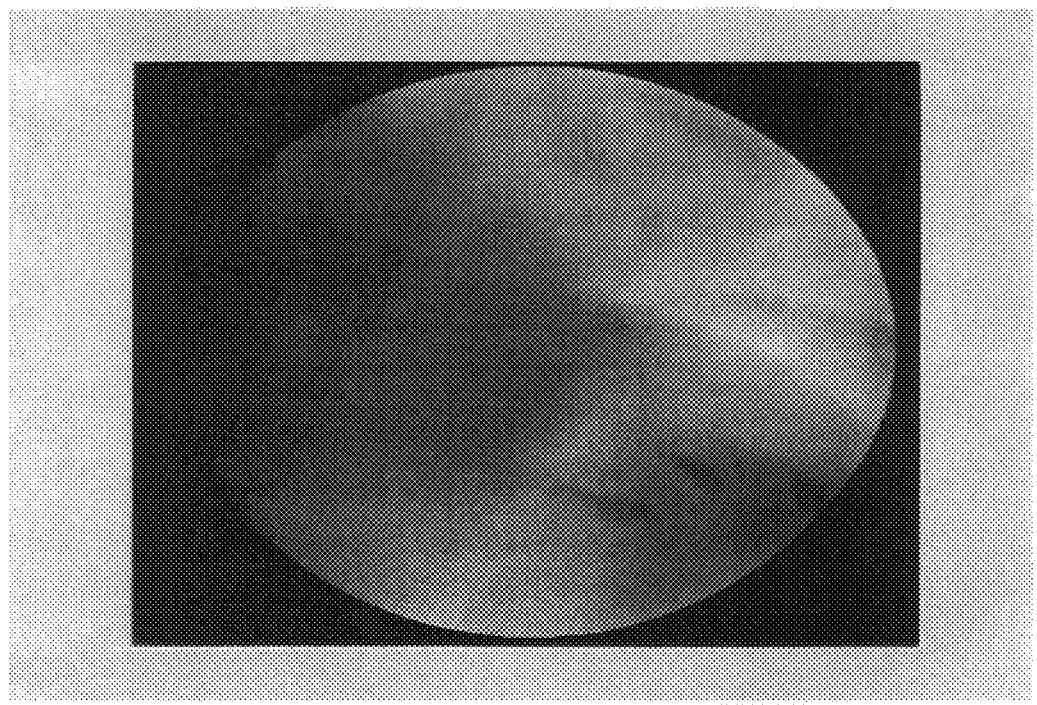
FIG. 15 is a partly enlarged view of FIG. 9.

"Cup jelly 10" and "Cup jelly 12" as shown in FIG. 9 are shown in FIG. 10–15 as the enlarged view , respectively.

Test Example 5
[Comparative test using water]

The similar procedure to Test Example 4 except for using about 20 mL of water in place of the swallowing-assistive drink was repeated. The results obtained are shown in FIG. 16–18.

Figure 16:
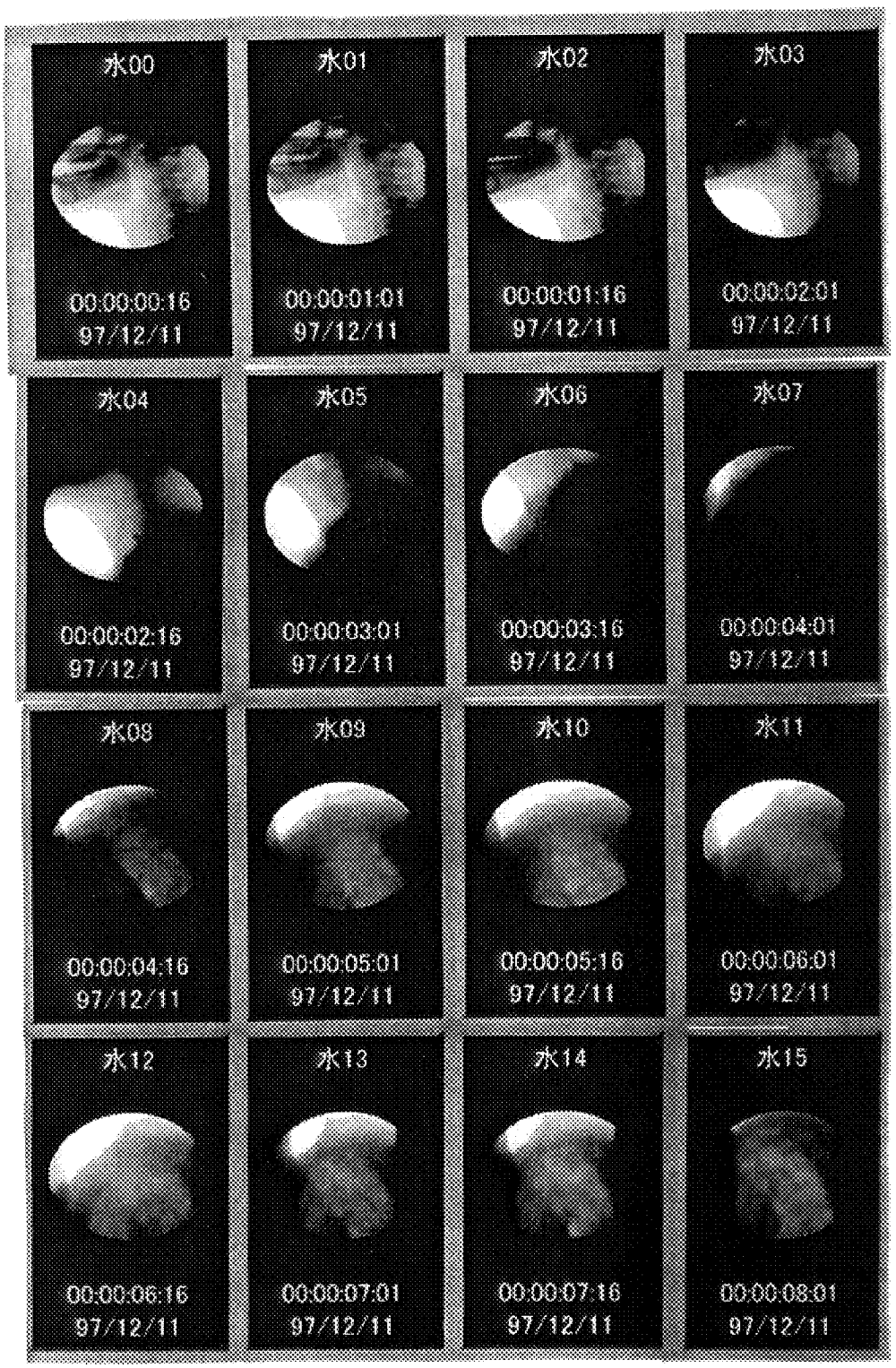
FIG. 16 shows still picture data showing the condition of taking in Test Example 5.
Figure 17:
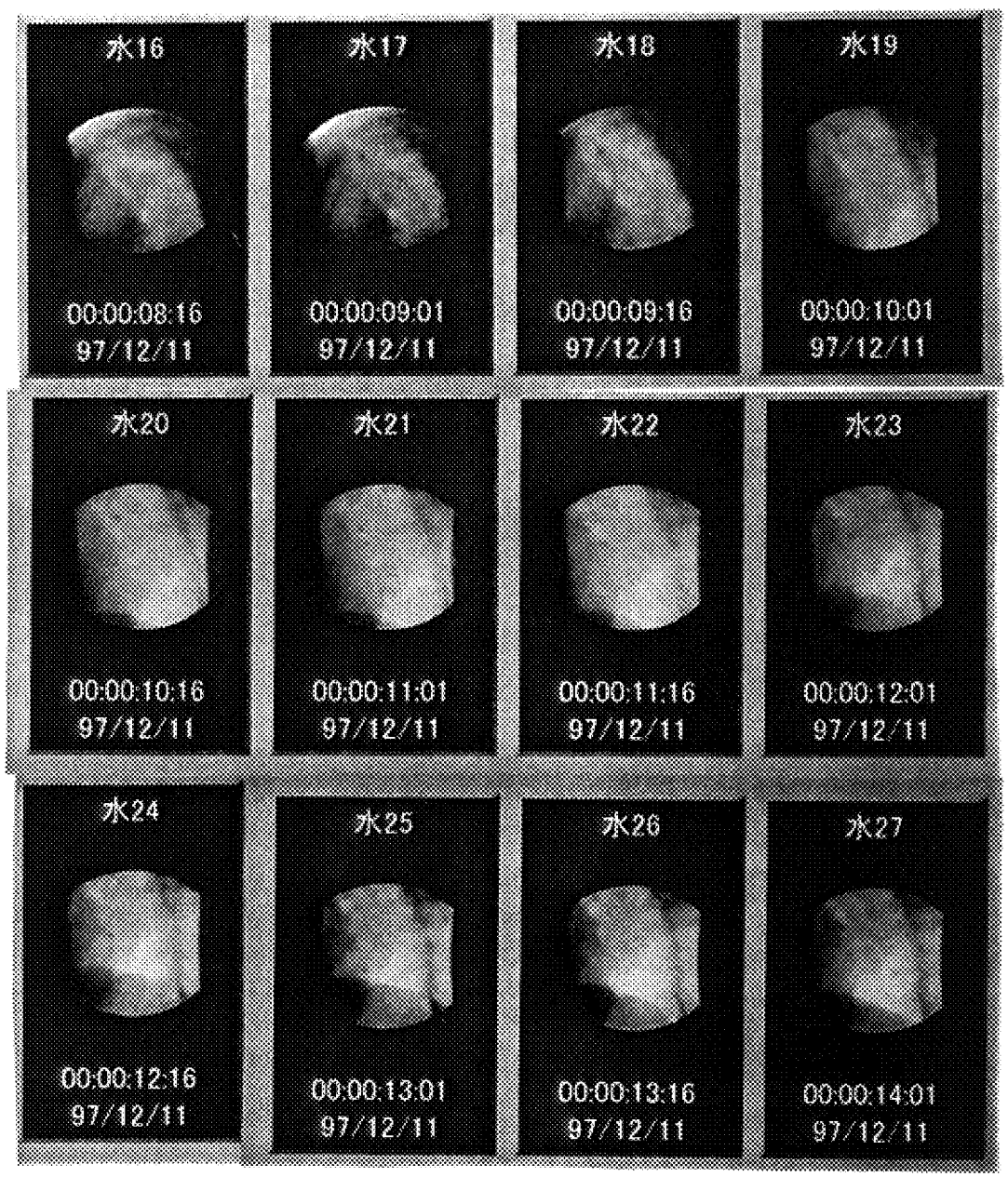
FIG. 17 shows still picture data showing the condition of taking in Test Example 5.
Figure 18:
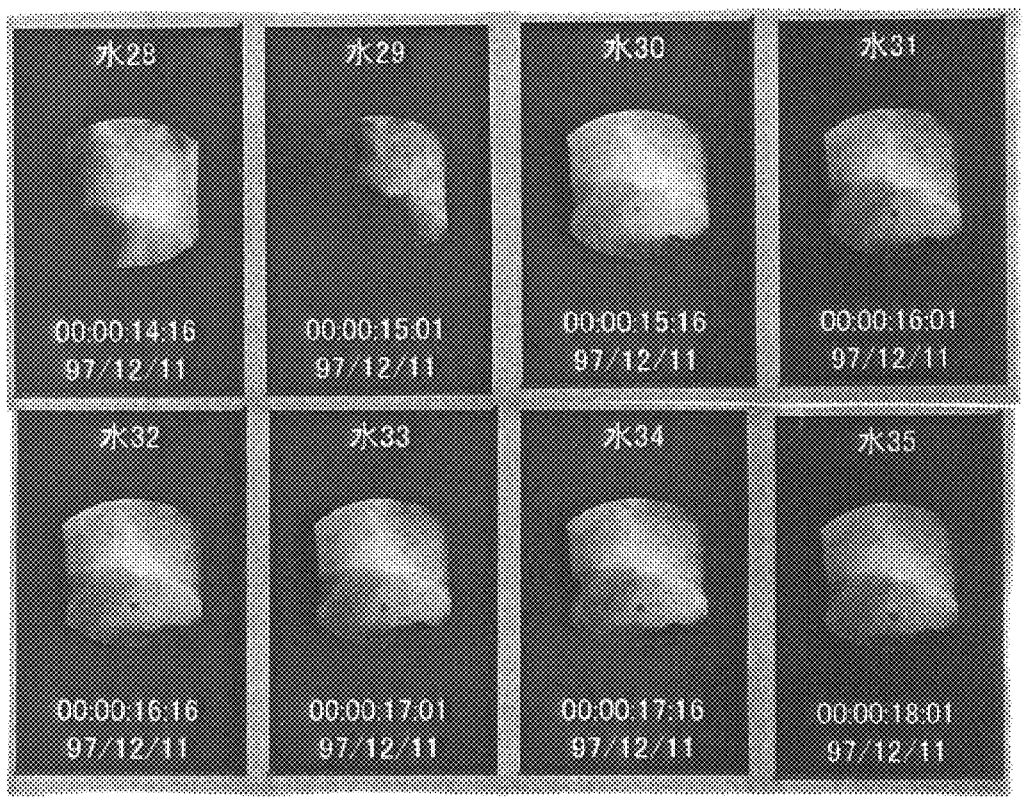
FIG. 18 shows still picture data showing the condition of taking in Test Example 5.
Figure 19:
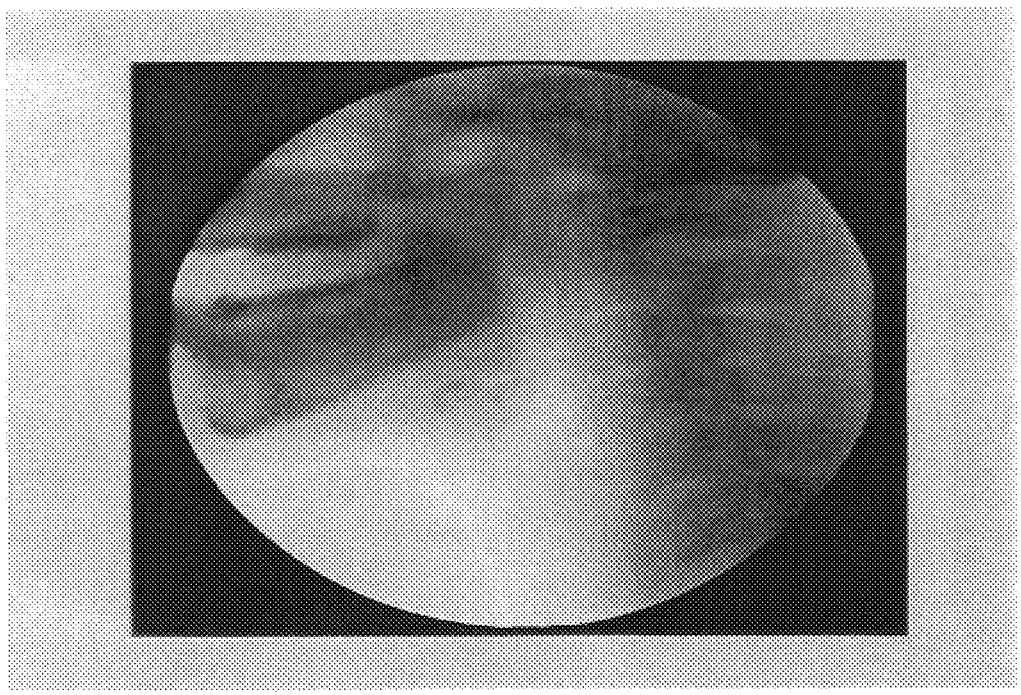
FIG. 19 is a partly enlarged view of FIG. 16.
Figure 20:
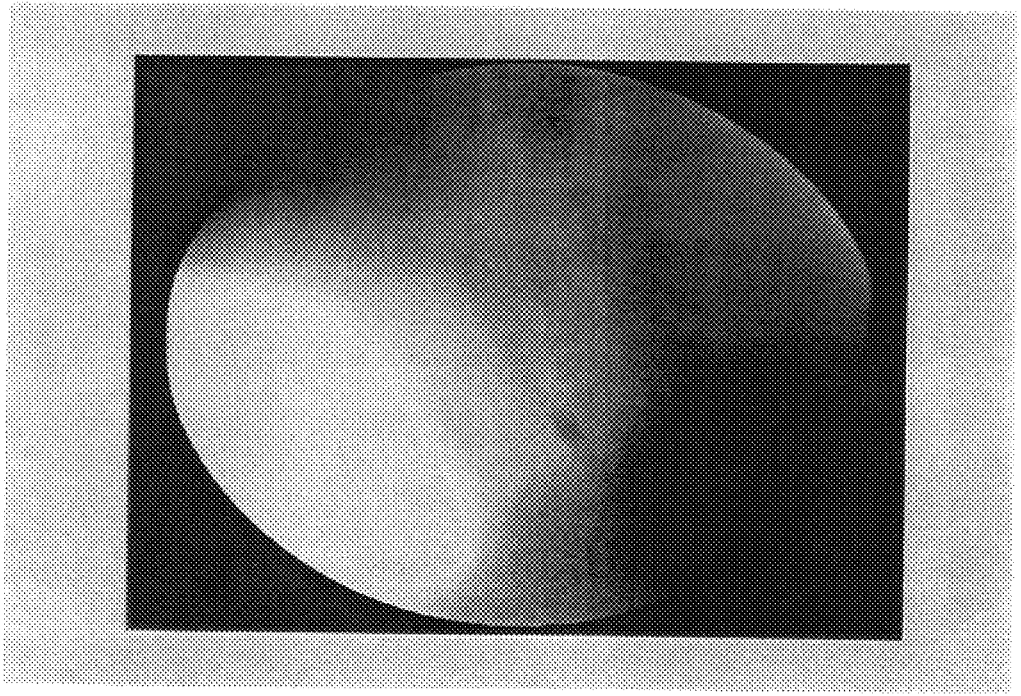
FIG. 20 is a partly enlarged view of FIG. 16.
Figure 21:
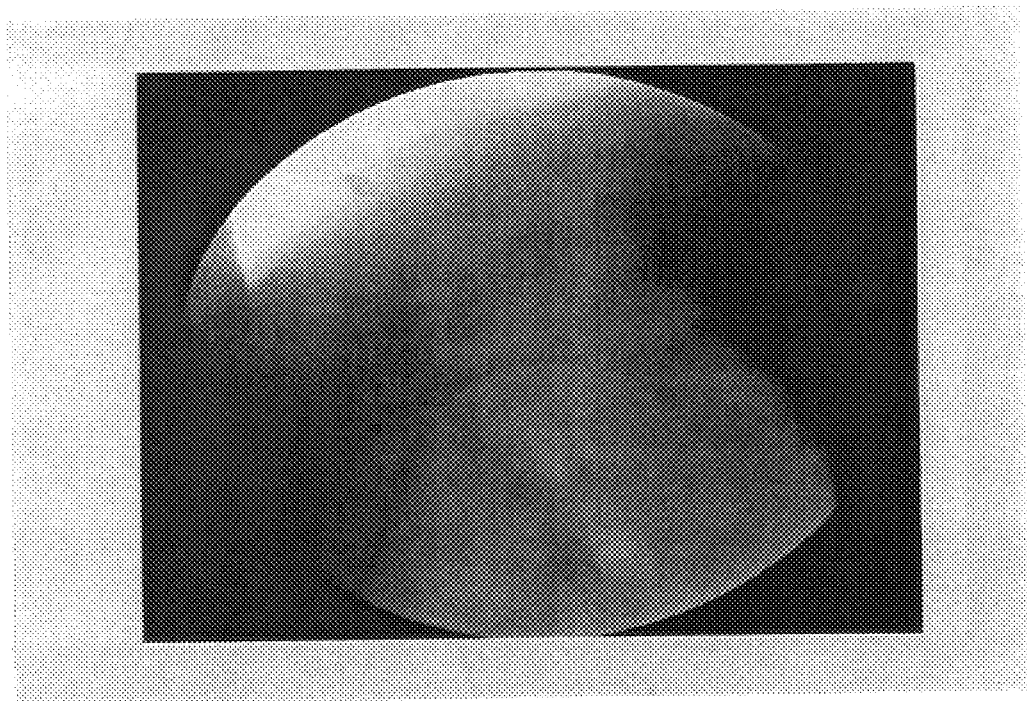
FIG. 21 is a partly enlarged view of FIG. 16.
Figure 22:
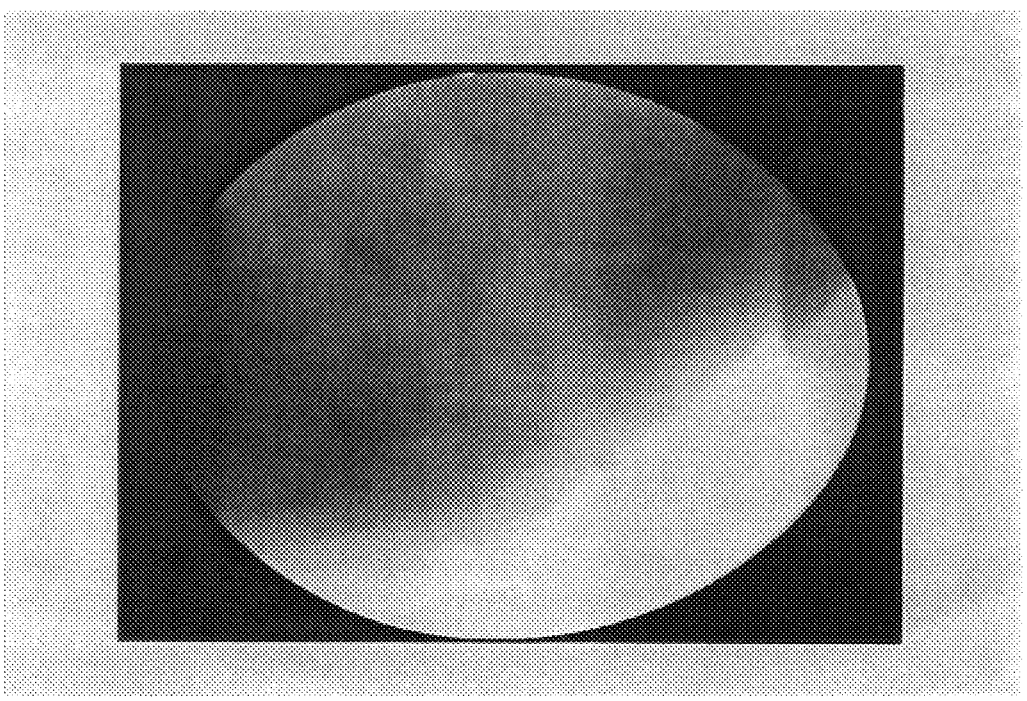
FIG. 22 is a partly enlarged view of FIG. 16.
Figure 23:
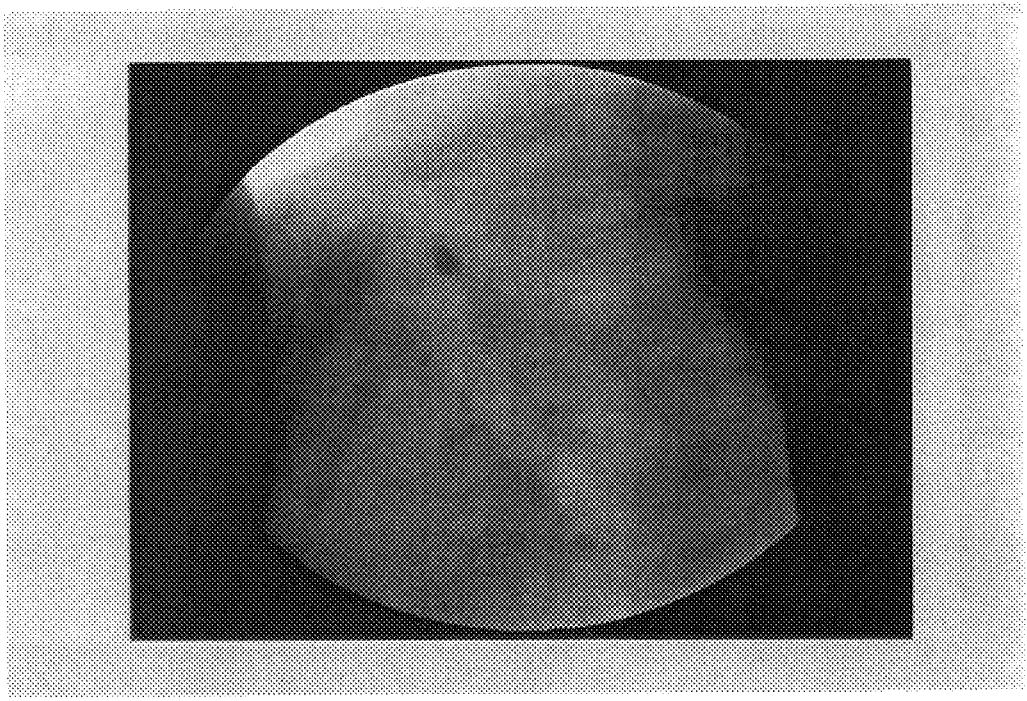
FIG. 23 is a partly enlarged view of FIG. 17.
Figure 24:
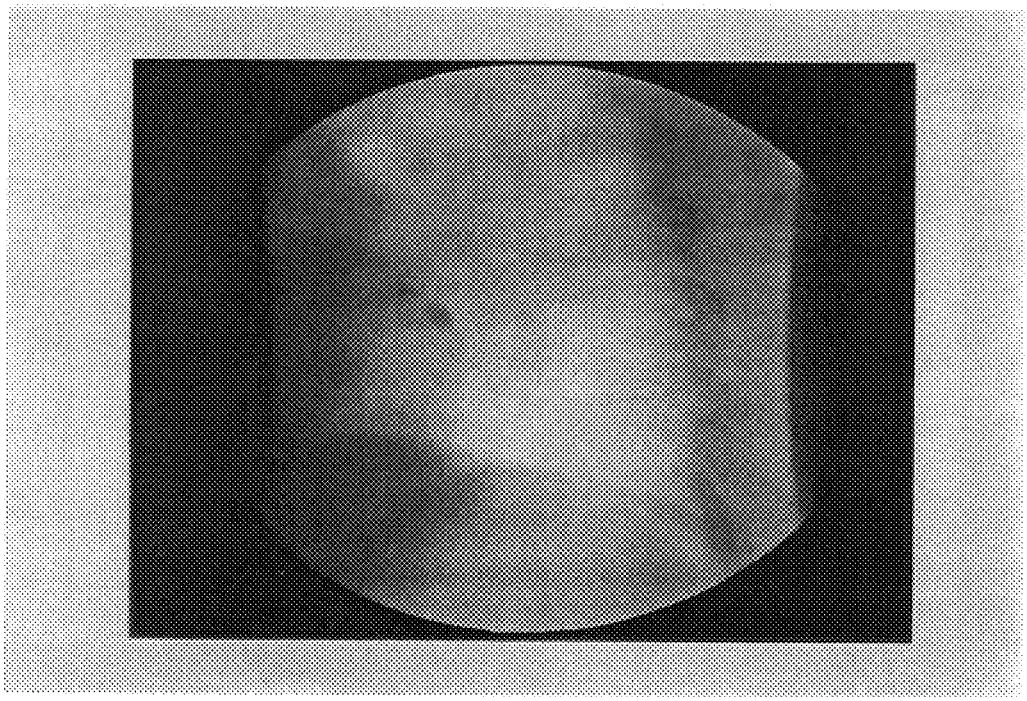
FIG. 24 is a partly enlarged view of FIG. 17.

Further, the enlarged still pictures of "Water 00," "Water 04," "Water 08," "Water 10," "Water 17" and "Water 24" as shown in FIG. 16–18 are shown in FIG. 19–24.

As obviously shown by comparing the results of Test Example 4 with those of Test Example 5, in Test Example 4 within the scope of the present invention, it takes about 8 sec to more for the mouth to the stomach, while it takes about 18 sec which is more than two times in Test Example 5, showing that the swallowing-assistive drink of the present invention gives an excellent swallowing-assistive effect.

As illustrated above, according to the present invention, by mixing specific adhesive pastes with water the swallowing-assistive drink for medicines that improves swallowing of various medicines, is convenient and substitutable with ordinary drinking water and does not disturb effectcacy of medicines and the method of swallowing can be provided.

Namely, patients who have difficulty in swallowing or who have a declined swallowing function, especially the aged patients can take medicines for internal use swallowing easily without having a sensation of foreign body by taking medicines orally together with the swallowing-assistive drink of the present invention.

Thus, the swallowing-assistive drink of the present invention improves the QOL (Quality of Life) of those who feel some pain when taking medicines and provides a help for their pleasant lives.

What is claimed is:

1. A swallowing-assistive drink for assisting an individual in swallowing a medication, the swallowing-assistive drink comprising:
    water and an adhesive paste which form a viscous liquid having a viscosity in the range of from 1,000–25,000 cP at 20° C.; and
    a medicine enwrapped in the viscous liquid.

2. The swallowing-assistive drink of claim 1 wherein the adhesive paste is at least one selected from the group consisting of agar, carrageenan, gellan gum, furcellaran, gelatin, pectin, curdlan, locust bean gum, tara gum, guar gum, xanthan gum, arginic acid, arginic acid salt, azotobacter vinelandi gum, cassia gum, psyllium seed gum, tamarind gum, CMCNa, CMCCa, whey protein starch and modified starch.

3. The swallowing-assistive drink of claim 1 wherein the swallowing-assistive drink contains in the range of from 0.1–5.0 wt % adhesive paste and in the range of from 80.0–99.9 wt % water.

4. The swallowing-assistive drink of claim 1 wherein the medicine is at least one of a tablet, a capsule, a granule, and powder.

5. The swallowing-assistive drink of claim 1 wherein the medicine is a mixture of solid formulations and at least one of granules and powder.

6. A swallowing-assistive drink for helping an individual swallow a medication, the swallowing-assistive drink comprising:
    water and an adhesive paste which forms a gelatinoid having a jelly strength in the range of from 10–100 g/cm$^2$ at 20° C.; and
    a medicine enwrapped in the gelatinoid.

7. The swallowing-assistive drink of claim 6 wherein the adhesive paste is at least one selected from the group consisting of agar, carrageenan, gellan gum, furcellaran, gelatin, pectin, curdlan, locust bean gum, tara gum, guar gum, xanthan gum, arginic acid, arginic acid salt, azotobacter vinelandi gum, cassia gum, psyllium seed gum, tamarind gum, CMCNa, CMCCa, whey protein starch and modified starch.

8. The swallowing-assistive drink of claim 6 wherein the swallowing-assistive drink contains in the range of from 0.1–5.0 wt % adhesive paste and in the range of from 80.0–99.9 wt % water.

9. The swallowing-assistive drink of claim 6 wherein the medicine is at least one of a tablet, a capsule, a granule, and powder.

10. The swallowing-assistive drink of claim 6 wherein the medicine is a mixture of solid formulations and at least one of granules and powder.

11. A method for assisting an individual in taking a medicine by swallowing the medicine, the method comprising the steps of:
    (a) providing a swallowing-assistive drink containing water and an adhesive paste which forms a viscous liquid having a viscosity in the range of from 1,000–25,000 cP at 20° C.; and
    (b) enwrapping the medicine in the viscous liquid.

12. The method of claim 11 wherein step (b) comprises enwrapping at least one of a tablet, a capsule, a granule, and powder in the viscous liquid.

13. A method for assisting an individual in taking a medicine by swallowing the medicine, the method comprising the steps of:
    (a) providing a swallowing-assistive drink containing water and an adhesive paste which forms a gelatinoid having a jelly strength in the range of from 10–100 g/cm$^2$ at 20° C.; and
    (b) enwrapping the medicine in the gelatinoid.

14. The method of claim 13 wherein step (b) comprises enwrapping at least one of a tablet, a capsule, a granule, and powder in the gelatinoid.

* * * * *